(12) United States Patent
Vaillancourt

(10) Patent No.: US 8,556,853 B2
(45) Date of Patent: *Oct. 15, 2013

(54) NEEDLE GUARD

(75) Inventors: Vincent L. Vaillancourt, Livingston, NJ (US); Patricia Vaillancourt, legal representative, Livingston, NJ (US)

(73) Assignee: Michael J. Vaillancourt, Chester, NJ (US)

(*) Notice: Subject to any disclaimer, the term of this patent is extended or adjusted under 35 U.S.C. 154(b) by 766 days.

This patent is subject to a terminal disclaimer.

(21) Appl. No.: 12/321,900

(22) Filed: Jan. 27, 2009

(65) Prior Publication Data

US 2009/0292260 A1 Nov. 26, 2009

Related U.S. Application Data

(60) Continuation of application No. 10/773,538, filed on Feb. 6, 2004, now Pat. No. 7,722,564, which is a division of application No. 10/116,776, filed on Apr. 4, 2002, now Pat. No. 6,761,706.

(60) Provisional application No. 60/280,991, filed on Apr. 4, 2001.

(51) Int. Cl.
*A61M 5/00* (2006.01)
*A61M 5/32* (2006.01)

(52) U.S. Cl.
USPC ........... 604/110; 128/919; 604/192; 604/198; 604/263

(58) Field of Classification Search
USPC ........... 604/263, 192, 110, 198, 195; 128/919
See application file for complete search history.

(56) References Cited

U.S. PATENT DOCUMENTS 5,894,015 A * 4/1999 Rechtin .......................... 422/301
6,234,999 B1 * 5/2001 Wemmert et al. ............. 604/162

* cited by examiner

*Primary Examiner* — Kevin C Sirmons
*Assistant Examiner* — Shefali Patel
(74) *Attorney, Agent, or Firm* — Francis C. Hand; Carella, Byrne et al

(57) ABSTRACT

A needle guard is attached to a needle hub by a polyester film strip and a needle passes through longitudinally spaced apart apertures in the strip. The film strip is housed in the needle guard in a corrugated manner. When the needle guard is pulled over the needle, the needle moves into a housing of the needle guard and into abutment with the housing while the strip is stretched between the hub and the housing to retain the housing connected to the hub under a biasing force.

5 Claims, 6 Drawing Sheets

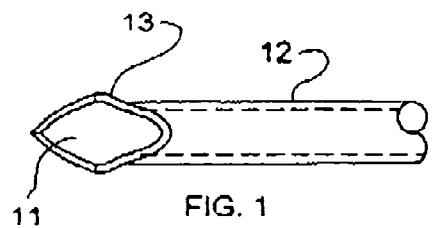
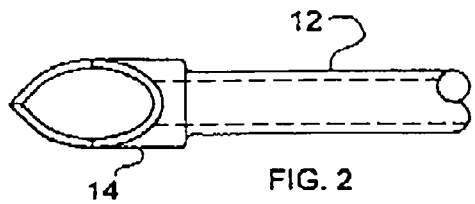
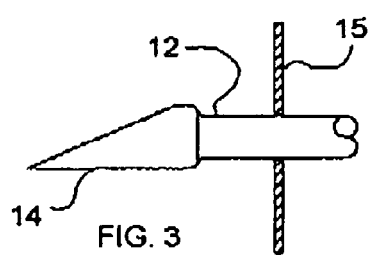
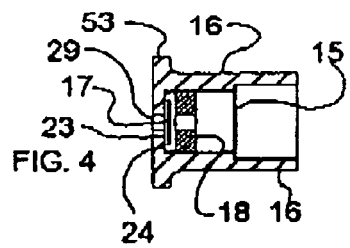
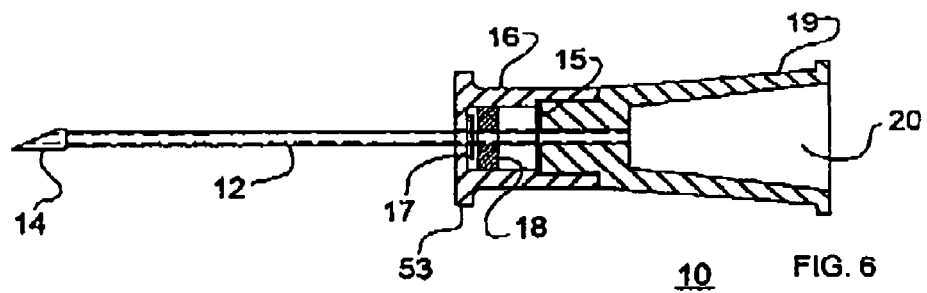
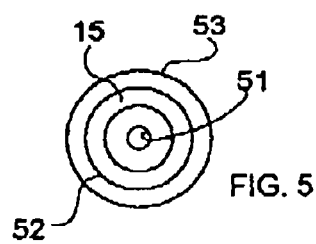

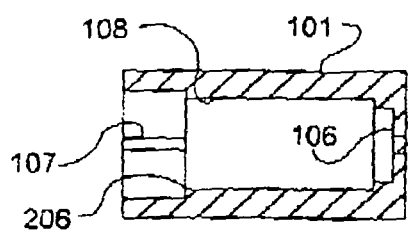
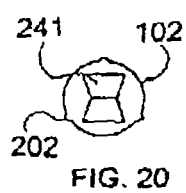
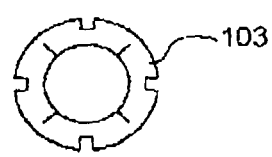
FIG. 19　　FIG. 20　　FIG. 21
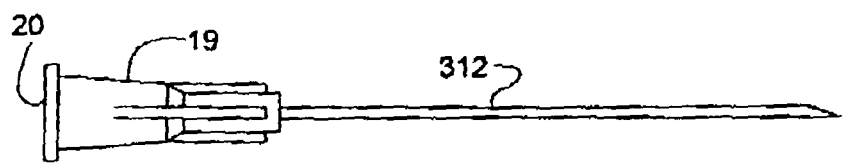
FIG. 22
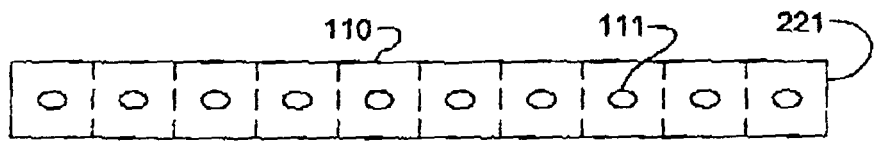
FIG. 23

NEEDLE GUARD

This application is a continuation of application Ser. No. 10/773,538, filed Feb. 6, 2004 (now U.S. Pat. No. 7,722,564) that is a division of Ser. No. 10/116,776, filed Apr. 4, 2002 (now U.S. Pat. No. 6,761,706) claiming the benefit of U.S. Provisional Application 60/280,991, filed Apr. 4, 2001.

This invention relates to a needle guard. More particularly this invention relates to a needle guard which encloses a sharpened needle edge either during the procedure for inserting a catheter or the like in a patient or upon removal of a sharpened needle after use from a patient.

As is well known, one major problem with hypodermic needles is the threat of cutting oneself or another person thereby potentially exposing blood to the environment. This has become especially important in a hospital atmosphere where AIDS patients or AIDS members of a staff can infect others by having their blood exposed and interact, for example by touching another person.

Various techniques have been proposed to overcome this problem. For example, in some cases, use has been made of a shield or cap which is placed over a needle after use. Generally, this is intended to only allow a one time use of the needle with an automatic covering system which prevents further use. However, during actual use of such a needle the needle does not remain totally protected. Further, if the needle is reused, there is no provision to sheath the needle.

Retractable syringe type needles are based on retracting the needle into the syringe upon completion of a fluid infusion procedure. A major problem with these types of products concerns the exit of the needle from the patient's skin. From the point of removal of the needle from the skin until the needle sharpened point enters the syringe barrel it is exposed to the environment with potential for needle sticks. There is also no provision for being able to switch needles on the syringe, that is one for infusing the fluid into the syringe, and a second for infusion into the patient. This is a very common practice.

U.S. Pat. No. 4,629,453 describes a protection device for a hypodermic needle which uses a protective cap which can be fitted over the needle when the needle is not in use.

U.S. Pat. No. 4,735,618 describes a protective enclosure for hypodermic needles which employ a cap-like needle guard which is positioned about a free end of a needle while being connected via collapsible arms to a rubber tubular sleeve mounted about a needle housing. When in use, the cap is pressed against a patient under a sufficient force to cause collapsing of the collapsible arms so that the cap slides back over the needle. However, when not intended for use, any accidental pushing in on the cap can cause an inadvertent needle stick.

SUMMARY OF THE INVENTION

The subject invention is directed to a needle guard mounted on a needle cannula. This needle guard can be moved from a first position where the sharpened edge of the needle is exposed for use to a second position where the tip of the sharpened needle is substantially enclosed.

The needle guard of the subject invention consists of a plastic sleeve housing having a proximal and distal end. The proximal end includes an opening into which is secured a metal part having a central hole. This central hole is sized to be just larger than the needle cannula diameter. The distal end of the needle guard consists of a circular opening which is larger than the needle cannula diameter. Inside the needle guard at the distal end is a washer having a central hole the size of the needle cannula and a diameter smaller than the inside diameter of the needle guard housing. The needle cannula is swaged, ground, or flared at the sharpened needle end to effectively increase the outer diameter or a portion thereof. This diameter is larger than the central hole of the metal part which is affixed to the proximal section of the needle guard.

Upon placement of a catheter or like structure when blood vessel puncture is achieved by the sharpened needle, the needle guard is gripped at the finger grips and moved in the distal direction until forward motion is stopped by the interference of the increased diameter area of the needle cannula and the central hole of the metal part located at the proximal end of the needle guard. The needle guard is designed such that prior to engagement of the enlarged diameter of the needle cannula with the smaller opening of the metal part, the sharpened needle passes into the needle guard and exits the opening of the washer. The washer moves in a direction parallel to it's surface thereby closing the tip portion of the needle guard and locking the sharpened needle within the needle guard.

The action is similar when an exposed needle is removed from a patient. At that time, the needle guard is moved forward to entrap the sharpened needle.

When used as an introducer needle (Seldinger technique), the guide wire after placement of the needle in the patient blood vessel is threaded through the needle into the blood vessel as conventional. The needle is removed from the patient and the needle guard immediately positioned over the needle tip. As the needle guard is now over the sharpened edge of the needle cannula, the user is protected from an inadvertent needle stick. However, the guide wire may continue to be threaded through the introducer needle similar to what is normally done when no safety guard is attached.

In another embodiment of this invention, the needle is conventional. At the proximal end of the plastic housing is secured a corrugated sleeve which in the pleated state has a central hole. The sleeve is threaded through the needle thereby opening up the corrugations. The last corrugation (pleat) is attached to the needle hub using a metal ring or other fastening device. The movement and locking of the needle within the plastic housing is similar to the embodiment previously described.

Accordingly, it is an object of this invention to provide a needle assembly with a protective needle guard to prevent needle sticks.

It is another object of this invention to provide a method for upsetting the needle cannula to achieve an enlarged section to act as a forward stop for the needle guard.

It is another object of this invention to provide a means for allowing a guide wire to be threaded through a sharpened needle in a "safe" condition.

It is an alternate another object of this invention to provide a corrugated strip whose axis is the needle and is strong and resilient to achieve the locking of the needle tip within the plastic housing.

These and other advantages will become more apparent from the following description taken in conjunction with the drawings wherein:

FIG. 1 illustrates a needle whose sharpened end has been flared to achieve an increase in effective diameter.

FIG. 2 illustrates a modified needle having an increased effective diameter at the sharpened end.

FIG. 3 illustrates the needle of FIG. 1 positioned near the forward lock showing the interference fit when the sharpened end of the needle comes in contact with the enlarged needle end.

FIG. 4 illustrates one embodiment of the plastic housing in cross section which contains the sharpened needle upon withdrawal of the needle from a patient.

FIG. 5 shows the proximal end view of the plastic housing of FIG. 4.

FIG. 6 illustrates the safety needle assembly in cross section ready to be used.

FIGS. 19, 20, 20A, 21, 22, 23, illustrates the components which make up the safety needle assembly shown in FIG. 24.

Figure 8:
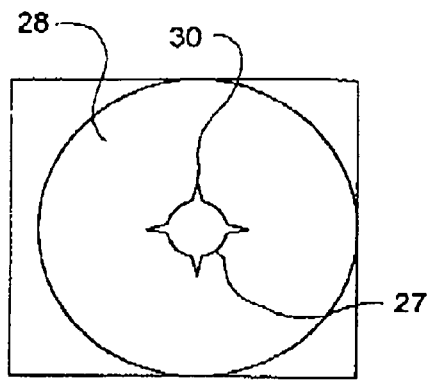
FIG. 8 is a detail of the forward locking member.

Referring to FIG. 4, the needle guard comprises a plastic hollow housing 16 having an opening at one end for passage of a needle; a lock ring 15 mounted in the housing 16 and having an aperture for passage of the needle therethrough; a centering washer 18 mounted in the housing 16 and having an aperture for passage of the needle therethrough; and a float washer 17 disposed in the housing 16 between the centering washer 18 and the end of the housing 16. The float washer 17 has an aperture for passage of the needle and is of a reduced size whereby upon withdrawal of the needle the float washer 17 moves out of alignment with the opening in the end of the housing 16 to block a return movement of the needle.

Referring to FIG. 1, the safety needle assembly consists of a sharpened hypodermic needle 12 with the sides of the beveled edge being flared 13. This flare increases the effective diameter of the needle by approximately 0.003"-0.005".

Referring to FIG. 2, the effective diameter 14 of the hypodermic needle 12 may also be increased just proximal to the sharpened portion of the needle. This may be achieved by swaging, grinding, or forming the needle 12 into an elliptical cross section proximal to the sharpened edge.

By way of example, in order to form an elliptical cross section, a mandrel may be inserted into a needle while a crimping tool applies a crimping force at two diametrically opposed areas of the outside of the needle. The mandrel serves to support the needle during the crimping operation in order to preserve the inside diameter of the needle while the crimping tool deforms the needle into an elliptical shape.

In FIG. 3, the outer diameter of the needle 12 just fits the opening of the forward lock ring 15 of the safety needle assembly. This forward lock ring 15 consists of a metal ring made of spring steel of approximately 0.005" in thickness with an aperture 51 sized to be slightly larger than the shank of the needle 12. For example, the needle 12 may be 0.042" in diameter and the aperture 51 0.043" in diameter. This differential in diameters is sufficient to compensate for tolerances and allow the plastic housing 16 to slide over the needle 12, and yet the interference is sufficient to lock the needle 12 distal to the metal ring 15.

Referring to FIG. 4 the metal forward lock ring 15 is secured in place within an internal shelf at the proximal end of the housing 16. The lock ring 15 can be secured by heat staking, ultrasonic welding, adhesive sealing, or the like (not shown).

The centering washer 18 acts as a guide to position the needle 12 within the housing. The float washer 17 is placed in the space created between the housing 16 interior face wall 23 and washer 18. A stop 24 (slight recess) in the housing 16 side wall positions the washer 18 such that there is sufficient space for the float washer 17 to move freely. One means by which this float washer 17 is positioned within the plastic housing 16 as shown is to place the centering washer 18 and float washer 17 on the needle 12 prior to assembly of the needle 12 to the needle hub 19.

FIG. 5 shows an end view of the plastic housing 16. It should be noted that in this view the smallest aperture 51 is that associated with the forward lock 15.

The safety needle assembly 10 (FIG. 6) is removably mounted on the hub 19 having a recess 20 to receive and attach to a syringe (not shown) just prior to use. Upon removal of the needle 12 from the patient after the injection-fluid transfer is completed, the plastic housing 16 is moved forward (distally) by the user until interference is achieved with the skin at which point the needle 12 is retracted from the patient and into the plastic housing 16. The forward lock 15 prevents the needle 12 from exiting the housing 16. Concurrently, as soon as the sharpened tip of the needle 12 enters the centering washer 18, the float washer 17 drops down and effectively seals off the housing aperture 29. In this manner the sharpened end of the needle 12 becomes trapped within the housing 16 preventing the user from being exposed to the sharpened edge of a needle 12 device.

Figure 7:
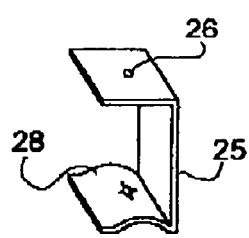
FIG. 7 illustrates a spring clip design containing the forward and rearward locking members.

The spring clip 25 (FIG. 7) contains both a forward lock 26 and rearward lock 28

Figure 11:
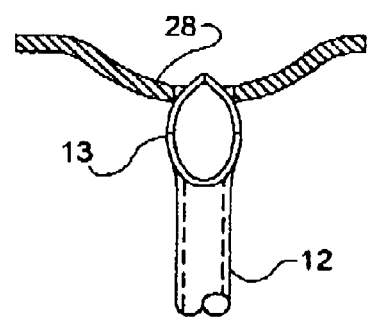
FIG. 11 illustrates in detail the means by which the needle is prevented from further forward movement once it encounters the locking member.

FIG. 8 and FIG. 11 refer to the operation of the rearward lock 28. The spring clip rearward lock 28 contains an aperture 27 through which the needle 12 moves. The four points 30 or cutouts provide sufficient bending to allow the needle 12 to retract into the housing 21 with minimum friction. When the needle sharpened tip 13 is retracted within the housing 21, the slightly flexed clip points 30 move back to their original non-flexed position decreasing the diameter of the aperture 27 of the rearward lock 28. When the needle 12 attempts to exit the housing 21 from within, the depression (see FIG. 11) is pushed forward further decreasing the size of the aperture 27 and preventing the needle 12 from exiting the housing 21.

Figure 9:
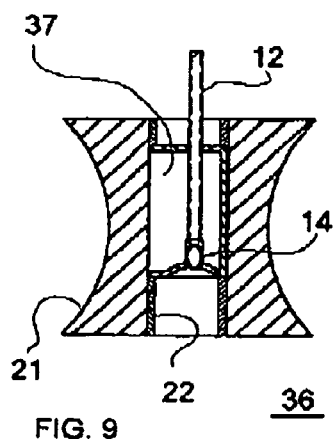
FIG. 9 illustrates the spring clip positioned within the plastic housing with the needle obstructed from forward movement.
Figure 10:
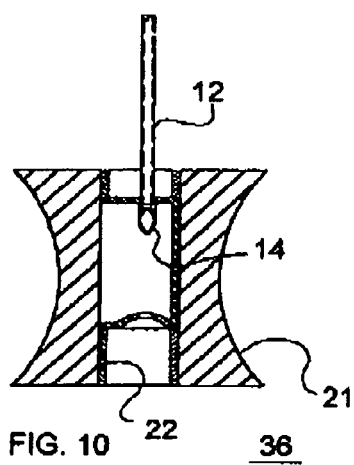
FIG. 10 illustrates the spring clip positioned within the plastic housing with the needle obstructed from rearward movement.

The needle 12 is shown locked in the forward lock FIG. 9 and rearward lock FIG. 10 positions. The spring clip 25 is placed within the housing 21. A spacer 22 having a slightly larger diameter than the housing 21 inner diameter secures the spring clip 25. A spacer may also be used at the opposite end or the housing 21 maybe molded with one end having a recess in which the spring clip may reside (not shown). The procedure used by the practitioner with this product is identical to that previously described for the first embodiment of this invention.

Figure 12:
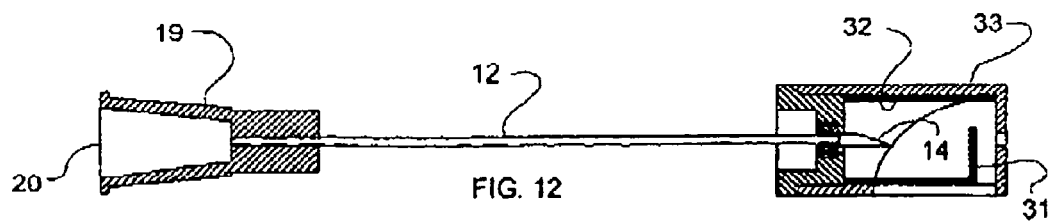
FIGS. 12, 13, 14, illustrates a needle assembly containing another embodiment of a spring clip to prevent forward movement upon retraction of the needle within the plastic housing.
Figure 13:
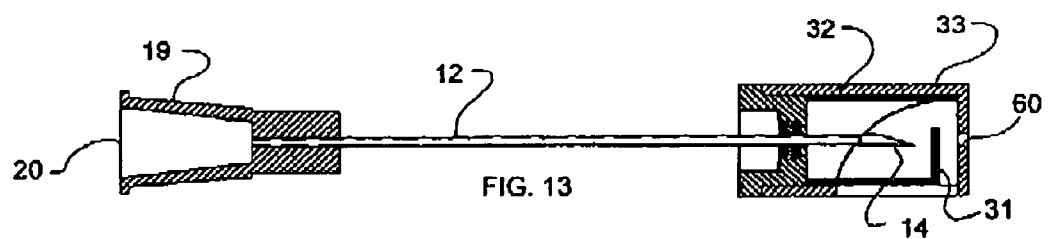
Figure 14:
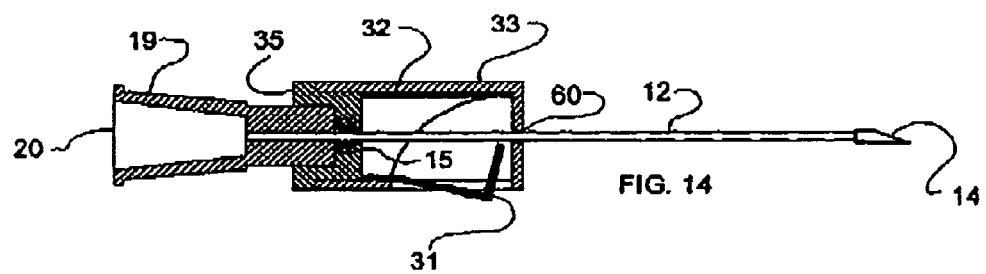
Figure 15:
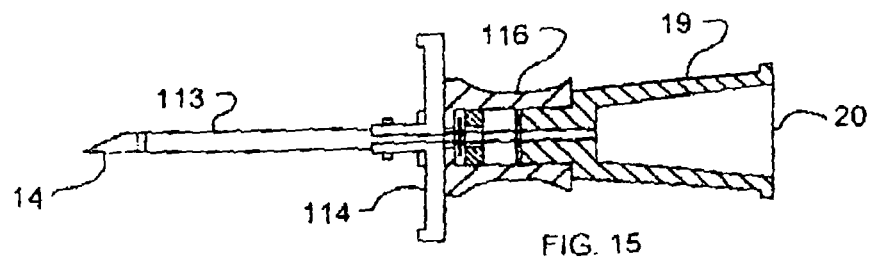
FIGS. 15, 16, 17 and 18 illustrate a needle catheter assembly utilizing the design shown in FIG. 6 but adapted to include a catheter on the distal portion of the needle.
Figure 16:
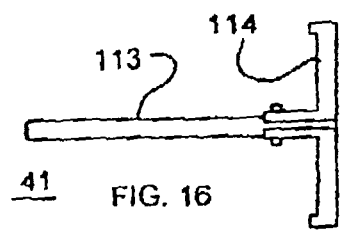
Figure 17:
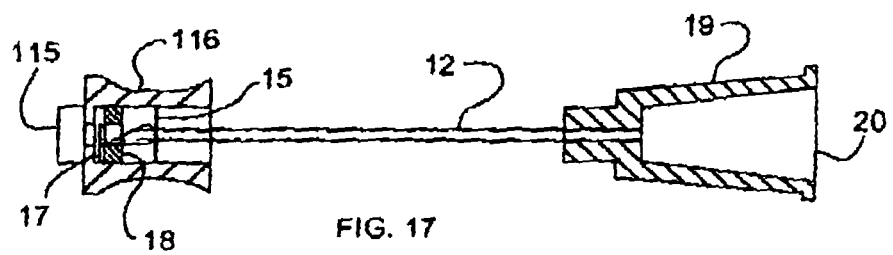
Figure 18:
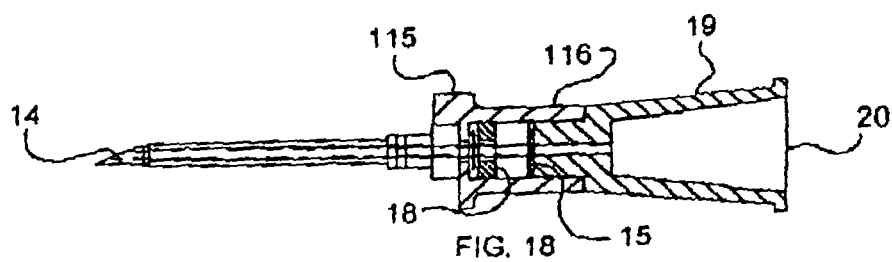
Figure 24:
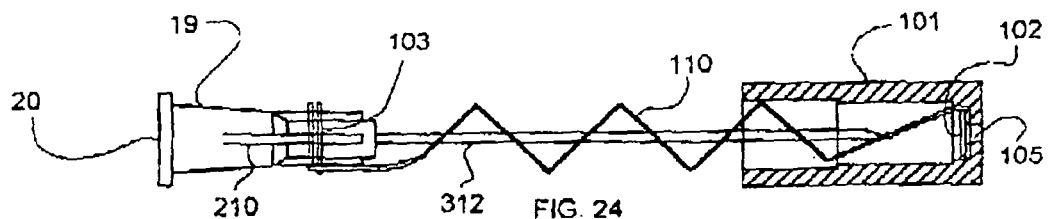
FIGS. 24, 25, 26, 27 illustrates a safety needle assembly having a corrugated strip attached to the plastic housing and needle hub to limit forward movement of the plastic housing.
Figure 25:
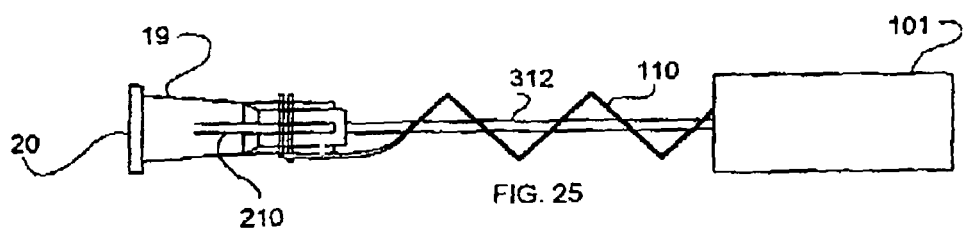
Figure 26:
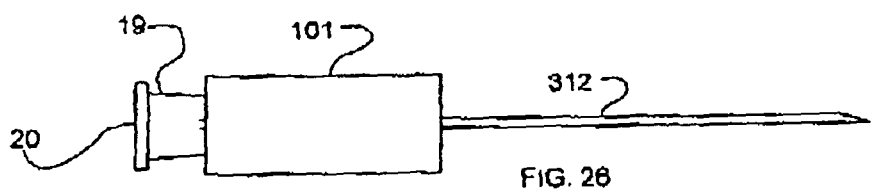

FIGS. 12, 13, and 14 refer to another embodiment of this invention. The use of the product and means for locking the needle 12 in the forward position is the same as previously described. The rearward locking component is composed of spring clip 31 which in its normal position presents a barrier to the needle 12 moving through the front face aperture 60 of the housing 33. When the housing is initially placed over the needle 12 axis the spring clip 31 is physically depressed to allow the needle 12 to move through the aperture 60 as shown in FIG. 14. In this condition, the spring clip 31 remains in a stressed state until the needle 12 is withdrawn into the housing 33 as seen in FIG. 12. The spring clip 31 may be circular in shape 32 for ease of insertion into the hollow housing 33.

FIGS. 15, 16, 17, 18 refer to another embodiment of the invention whereby a peel away sheath 41 is used in conjunction with the safety needle product (see FIG. 6). Upon grasping of the safety needle housing 116 by the user and retracting the needle hub 19 the needle 12 with sharpened tip 14 enters the peel away sheath 41. Upon further withdrawal of the needle hub 19 the needle sharpened tip 14 enters and is locked in the safety needle housing 116. The peel away sheath 41 remains within the body cavity (not shown) and is ready for insertion of a suitable catheter, guidewire, or the like. The peel away sheath 41 may be a catheter, dilator or the like. The porch or overhang 115 stabilizes the wings 114 of the peel away sheath 41 to prevent circular movement about the axis of the needle 12 during the insertion procedure and removal of the needle 12. Although the tip of the needle 14 appears to interfere with the inner diameter of the sheath lumen 113, in practice, due to the relatively small difference in diameter of the two parts and the fact the sheath 113 is plastic, there is no problem in moving the needle 12 through the sheath 113.

FIGS. 19, 20, 20A, 21, 22, 23, refer to the components of the safety needle assembly depicted in FIGS. 24,25,26,27. The safety needle housing 101 shown in cross section consists of a generally tubular construction with an aperture 105 at one end and with the inner hollowed out portion 108 having two recesses 106 and 206. Into the first recess 106 is positioned the stainless steel washer 102. The washer 102 outer diameter points 202 are slightly larger than the recess 106 diameter. The points 202 bite into the plastic wall creating an effective seal of the washer 102 to the housing 101.

Figure 27:
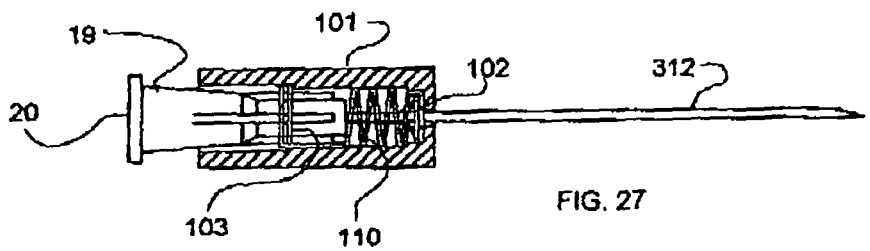
Figure 20A:
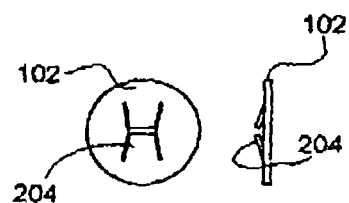

The Mylar (polyester film) strip 110 is corrugated as shown in FIG. 27 and has a series of longitudinally spaced apart apertures 111 (FIG. 23). The end or first corrugation 221 is placed behind the washer 102, that is, between the face wall 104 of the housing 101 prior to locking the washer 102 in place. The compressed corrugated Mylar strip 110 is placed within the housing 101. Just in front of the last corrugation is placed the hub locking washer 103. This washer 103 is placed in the rear recess 206 with the four cutouts of the washer 103 positioned over the four splines 107 of the safety needle housing 101. This washer 103 is pushed or otherwise positioned over the needle hub 20 splines 210 to form an interference fit between the washer 103 and the needle hub 20.

The fitment of the washer 103 over the safety needle housing splines 107 is sufficient that the housing 101 may be gripped and used to wrench the needle hub 20 onto a male luer connector (not shown). The clearance between the washer 103 outer ring is such that when the safety needle housing 101 is moved forward, the housing 101 will readily separate from the washer 103 leaving the Mylar strip 110 connected to the needle hub 20.

As the safety needle housing 101 moves down the needle 12 axis, the Mylar strip 110 unfolds about the needle 12 until it reaches it's maximum extension. The Mylar strip's 110 length is such that the housing 101 will enclose the sharpened end of the needle 12 before full extension is obtained. When full extension of the Mylar strip 110 is obtained and the needle 12 is totally within the safety needle housing 101, the user releases the housing 101. At that time there is some retraction of the Mylar strip 110 pushing the needle 12 sharpened point against the "H" shaped lock 102. This lock 102 is initially flexed 204 inwardly by the movement of the needle 12 in the proximal direction through the housing 101.

When the needle 12 is retracted into the housing 101 the washer flaps 241 close and regain their initial shape. The "H" section 102 is prevented from moving in the opposite direction (outward) by the front wall of the housing 101 which interferes with any potential movement of the flaps 241.

It has been found that a maximum force of less than ten pounds is exerted by the user when moving the safety needle housing 101 to the extended position. A Mylar strip 110 having a width of 0.30" and a thickness of 0.004" and holes to accommodate an 18 Ga. Needle will withstand a force greater than 15 pounds. Using a 0.010" thick locking washer 103 with an inner diameter slightly smaller than the outer effective diameter of the needle hub splines will secure the Mylar strip 110 with a breakaway force greater than fifteen pounds.

After use and the sharpened needle 312 point is secured within the safety needle housing 101, the product may be safely handled without concern for needle sticks by the user.

Major advantages of this product include the movement of the safety needle housing 101 into position before the needle is withdrawn from the patient. As a result the sharpened point is never exposed. Although not shown a guard in the form of a flange maybe placed at the distal end of the safety needle housing to prevent accidental movement of the fingers beyond the distal end of the housing. The housing 101 may be dished along the outer portions length to provide a more positive grip for the user.

When a guidewire (not shown) is used such as in a Seldinger procedure the guidewire is positioned within the needle 312 and extended into the body cavity prior to activation of the safety needle housing 101. Upon activation the flaps 204 of the "H" washer 241 now enclose only the guidewire. However, the flaps have moved sufficiently to prevent the needle 312 from exiting the safety needle housing as the opening is too small for the needle's 312 diameter. However, the guidewire maybe moved independent of the location of the needle 312 until it retracts beyond the location of the flaps of the "H" washer 241. Hence the safety needle housing does not restrict freedom of movement of the guidewire even after the sharpened edge of the needle 312 is safely positioned within the housing 101.

What is claimed is:

1. In combination,
a hub;
a needle secured to and extending from said hub and having a sharpened end for insertion in a patient;
a needle housing removably mounted on said hub, said needle housing having an aperture at one end with said needle passing therethrough;
a polyester film strip secured to and between said hub and said housing, said strip having a series of longitudinally spaced apart apertures receiving said needle therein and being disposed in corrugated relation between said hub and said housing whereby before said needle is withdrawn from the patient said housing is movable from said hub over said needle while said strip extends between said hub and said housing and as said needle is withdrawn from the patient said housing is movable beyond said sharpened end of said needle while said strip is stretched to an extended state between said hub and said housing and upon release of said housing said strip is retracted to return said housing towards said sharpened end of said needle to retain said housing connected to said hub under a biasing force in said strip directing said housing towards said hub; and a flat washer mounted in said housing to secure one end of said strip to said housing whereby upon retraction of said strip said sharpened end of said needle abuts said washer.

2. The combination as set forth in claim 1 wherein said strip is corrugated.

3. The combination as set forth in claim 1 wherein said strip has a width of 0.30 inches and a thickness of 0.004 inches.

4. The combination as set forth in claim 1 wherein said washer has flaps defining an aperture for passage of said needle therethrough whereby in response to withdrawal of said needle through said aperture of said washer said flaps flex inwardly to block a return passage of said needle through said aperture of said washer.

5. The combination as set forth in claim 1 wherein said strip extends to a length in said extended state thereof greater than an extent of said needle from said hub to allow said housing to be moved beyond said sharpened end of said needle before retraction of said strip.

* * * * *